(12) United States Patent
Wachirajindakul et al.

(10) Patent No.: US 12,383,792 B2
(45) Date of Patent: *Aug. 12, 2025

(54) RANK LISTING OF COMPETITIVE PERFORMANCES OF EXERCISE ON A MACHINE

(71) Applicant: Hydrow, Inc., Cambridge, MA (US)

(72) Inventors: Non Wachirajindakul, Cambridge, MA (US); Christopher Francois Paul, Lincoln, MA (US)

(73) Assignee: Hydrow, Inc., Boston, MA (US)

( * ) Notice: Subject to any disclaimer, the term of this patent is extended or adjusted under 35 U.S.C. 154(b) by 48 days.

This patent is subject to a terminal disclaimer.

(21) Appl. No.: 17/582,951

(22) Filed: Jan. 24, 2022

(65) Prior Publication Data

US 2022/0143465 A1     May 12, 2022

Related U.S. Application Data

(63) Continuation of application No. 17/001,285, filed on Aug. 24, 2020, now Pat. No. 11,229,825.

(51) Int. Cl.
*A63B 24/00*        (2006.01)
*A63B 71/06*        (2006.01)

(52) U.S. Cl.
CPC ...... *A63B 24/0062* (2013.01); *A63B 24/0003* (2013.01); *A63B 24/0006* (2013.01);
(Continued)

(58) Field of Classification Search
None
See application file for complete search history.

(56) References Cited

U.S. PATENT DOCUMENTS

| 2,002 | A | 3/1841 | Rider |
| 3,912,264 | A | 10/1975 | Busse et al. |

(Continued)

FOREIGN PATENT DOCUMENTS

| CN | 1484538 | 3/2004 |
| CN | 101234224 | 8/2008 |

(Continued)

OTHER PUBLICATIONS

How the Leaderboard Works, Jul. 30, 2019, Hydrow, 1-4 https://support.hydrow.com/hc/en-us/articles/360031429651-How-the-Leaderboard-Works (Year: 2019).*

(Continued)

*Primary Examiner* — Shila Jalalzadeh Abyaneh
(74) *Attorney, Agent, or Firm* — Fish & Richardson P.C.

(57) ABSTRACT

Among other things, a processor executes instructions to: update, in real time during a current instance of an exercise activity by a subject competitor, a graphical user interface displayed on a display device, the display device being included in a first exercise machine operated by the subject competitor or included in a mobile electronic device. The graphical user interface includes: a ranking of the subject competitor and a second competitor based on (i) a projected performance metric of the subject competitor over a predefined scope of the exercise activity compared to (ii) a historical performance metric of the second competitor over the predefined scope of the exercise activity in a previous instance of the exercise activity, an illustration of a margin between the historical performance metric of the second competitor and the projected performance metric for the subject competitor, and an illustration of the projected performance metric.

12 Claims, 3 Drawing Sheets

Figure 1:
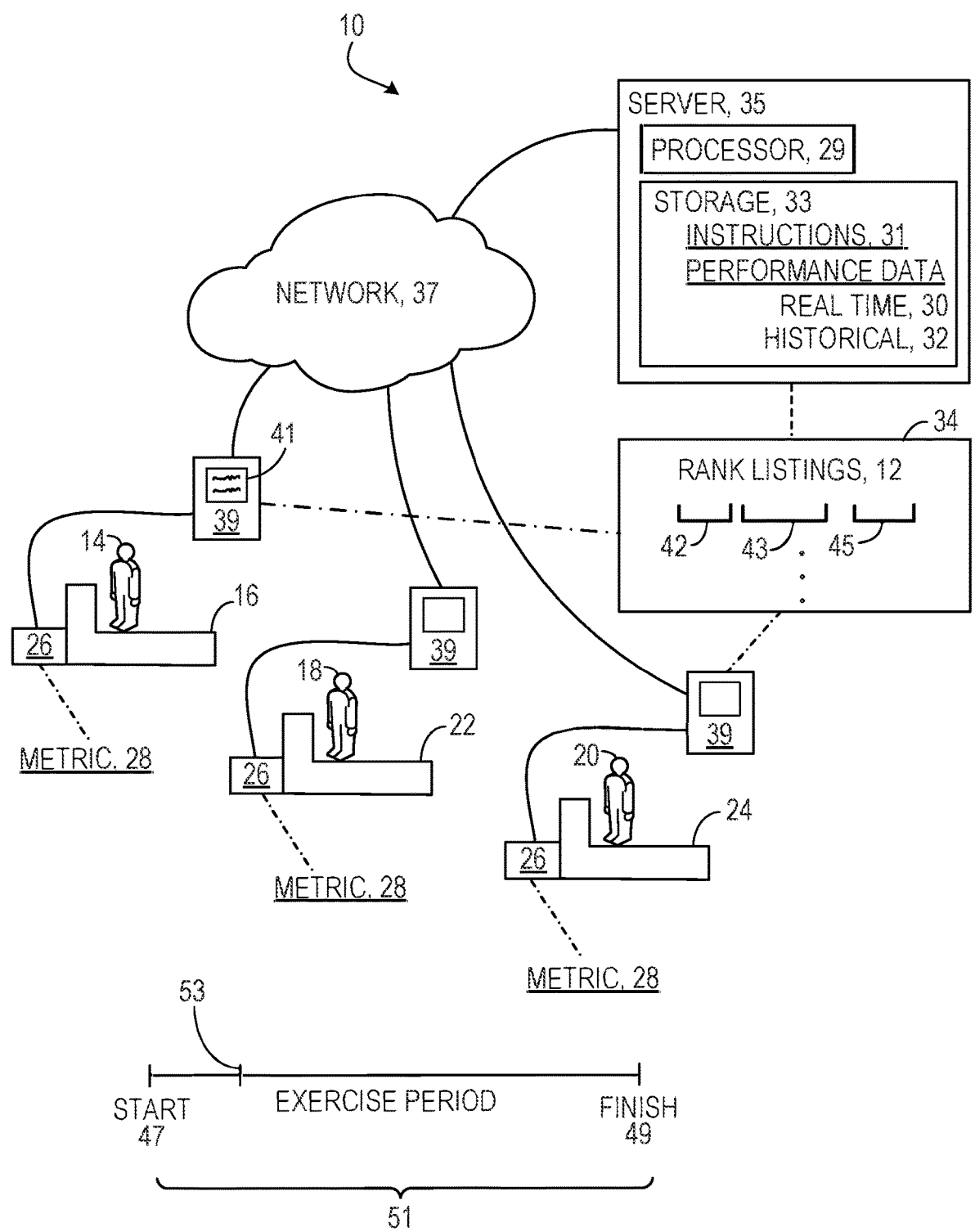

(52) U.S. Cl.
CPC .......... *A63B 24/0075* (2013.01); *A63B 71/06* (2013.01); *A63B 71/0616* (2013.01); *A63B 2024/0015* (2013.01); *A63B 2024/0065* (2013.01); *A63B 2024/0068* (2013.01); *A63B 2024/0081* (2013.01)

(56) References Cited

U.S. PATENT DOCUMENTS

| | | |
|---|---|---|
| 4,735,410 A | 4/1988 | Nobuta |
| 4,798,378 A | 1/1989 | Jones |
| 4,984,986 A | 1/1991 | Vohnout |
| 5,076,573 A | 12/1991 | Lo |
| 5,409,435 A | 4/1995 | Daniels |
| 5,466,200 A | 11/1995 | Ulrich et al. |
| 5,656,001 A | 8/1997 | Baatz |
| 5,772,560 A | 6/1998 | Watterson et al. |
| 6,447,424 B1 | 9/2002 | Ashby et al. |
| 6,601,016 B1 | 7/2003 | Brown et al. |
| 6,626,799 B2 | 9/2003 | Watterson et al. |
| 6,701,271 B2 | 3/2004 | Willner et al. |
| 6,749,537 B1 | 6/2004 | Hickman |
| 6,808,472 B1 | 10/2004 | Hickman |
| 6,902,513 B1 | 6/2005 | McClure |
| 6,921,351 B1 | 7/2005 | Hickman et al. |
| 6,945,917 B1 | 9/2005 | Baatz |
| 7,166,064 B2 | 1/2007 | Watterson et al. |
| 7,311,640 B2 | 12/2007 | Baatz |
| 7,556,590 B2 | 7/2009 | Watterson et al. |
| 7,628,730 B1 | 12/2009 | Watterson et al. |
| 7,769,794 B2 | 8/2010 | Moore et al. |
| 7,874,957 B2 | 1/2011 | Hurwitz et al. |
| 7,946,961 B2 | 5/2011 | Blum et al. |
| 8,103,517 B2 | 1/2012 | Hinnebusch |
| 8,152,696 B2 | 4/2012 | Blum et al. |
| 8,409,057 B2 | 4/2013 | Martens |
| 8,622,876 B2 | 1/2014 | Kelliher |
| 8,684,888 B2 | 4/2014 | Blum et al. |
| 9,174,085 B2 | 11/2015 | Foley et al. |
| 9,233,276 B1 | 1/2016 | Foley et al. |
| 9,302,152 B2 | 4/2016 | Blum et al. |
| 9,861,855 B2 | 1/2018 | Foley et al. |
| 9,974,995 B2 | 5/2018 | Hall |
| 10,322,315 B2 | 6/2019 | Foley et al. |
| 10,471,297 B1 | 11/2019 | Smith et al. |
| 10,486,026 B2 | 11/2019 | Foley et al. |
| 10,610,725 B2 | 4/2020 | Schaefer et al. |
| 10,639,521 B2 | 5/2020 | Foley et al. |
| 10,828,531 B1 | 11/2020 | Smith et al. |
| 10,946,263 B2 | 3/2021 | Felker |
| 10,956,630 B2 | 3/2021 | Le Chevalier et al. |
| 11,130,017 B2 | 9/2021 | Smith et al. |
| 11,229,825 B1 | 1/2022 | Wachirajindakul et al. |
| 11,766,588 B2 | 9/2023 | Smith et al. |
| 11,904,200 B2 | 2/2024 | Smith et al. |
| 2005/0085348 A1 | 4/2005 | Kiefer et al. |
| 2005/0164833 A1 | 7/2005 | Florio |
| 2007/0219059 A1 | 9/2007 | Schwartz et al. |
| 2008/0005276 A1 | 1/2008 | Frederick |
| 2008/0052756 A1 | 2/2008 | Morishige et al. |
| 2008/0109158 A1 | 5/2008 | Huhtala et al. |
| 2008/0280736 A1 | 11/2008 | D'Eredita |
| 2009/0075782 A1 | 3/2009 | Joubert et al. |
| 2009/0164448 A1 | 6/2009 | Curtis |
| 2009/0233769 A1 | 9/2009 | Pryor |
| 2009/0291726 A1 | 11/2009 | Svensson |
| 2009/0291805 A1 | 11/2009 | Blum et al. |
| 2010/0144497 A1 | 6/2010 | Clark |
| 2010/0173749 A1 | 7/2010 | Lannon et al. |
| 2011/0082009 A1 | 4/2011 | Ranky et al. |
| 2011/0105281 A1 | 5/2011 | Jerichow |
| 2011/0201477 A1 | 8/2011 | Blum et al. |
| 2011/0245044 A1 | 10/2011 | Kelliher |
| 2012/0120771 A1 | 5/2012 | Lapides |
| 2012/0237910 A1 | 9/2012 | Blum et al. |
| 2013/0130206 A1 | 5/2013 | Smith et al. |
| 2013/0171594 A1* | 7/2013 | Gorman ................... G09B 5/00 434/219 |
| 2013/0274635 A1 | 10/2013 | Coza |
| 2014/0172135 A1* | 6/2014 | Eisner ................... G06F 17/40 700/91 |
| 2014/0244010 A1 | 8/2014 | Harvey |
| 2014/0337450 A1 | 11/2014 | Choudhary |
| 2015/0057130 A1 | 2/2015 | Lin et al. |
| 2015/0170530 A1 | 6/2015 | Damman et al. |
| 2015/0360083 A1 | 12/2015 | Lagree et al. |
| 2016/0107023 A1 | 4/2016 | Campanaro et al. |
| 2016/0158603 A1 | 6/2016 | Darwood et al. |
| 2016/0271441 A1 | 9/2016 | Hoover |
| 2016/0287939 A1 | 10/2016 | Deochand et al. |
| 2017/0319889 A1 | 11/2017 | Cei et al. |
| 2017/0319904 A1 | 11/2017 | Deochand et al. |
| 2017/0319906 A1 | 11/2017 | Chang et al. |
| 2018/0056132 A1 | 3/2018 | Foley et al. |
| 2018/0099178 A1 | 4/2018 | Schaefer |
| 2018/0126249 A1 | 5/2018 | Consiglio |
| 2018/0140903 A1 | 5/2018 | Poure et al. |
| 2018/0161658 A1 | 6/2018 | Felker |
| 2018/0214729 A1 | 8/2018 | Rubin et al. |
| 2018/0264366 A1 | 9/2018 | Kawahara |
| 2018/0285496 A1 | 10/2018 | Le Chevalier et al. |
| 2018/0339195 A1 | 11/2018 | Bernotas |
| 2019/0070448 A1 | 3/2019 | Jeremic et al. |
| 2019/0126099 A1 | 5/2019 | Hoang |
| 2019/0184234 A1 | 6/2019 | Packles et al. |
| 2019/0255386 A1 | 8/2019 | Trotter |
| 2019/0290964 A1 | 9/2019 | Oren |
| 2019/0336827 A1* | 11/2019 | Intonato ............. A63B 71/0622 |
| 2019/0351283 A1 | 11/2019 | Smith et al. |
| 2020/0078635 A1 | 3/2020 | Smith et al. |
| 2020/0376223 A1 | 12/2020 | Smith et al. |
| 2021/0060378 A1 | 3/2021 | Smith et al. |
| 2021/0402250 A1 | 12/2021 | Smith et al. |
| 2024/0082629 A1 | 3/2024 | Smith et al. |

FOREIGN PATENT DOCUMENTS

| | | |
|---|---|---|
| CN | 202179824 | 4/2012 |
| CN | 204219688 | 3/2015 |
| CN | 205699387 | 11/2016 |
| CN | 107970562 | 5/2018 |
| CN | 108096807 A | 6/2018 |
| CN | 110327587 | 10/2019 |
| EP | 0919259 | 6/1999 |
| TW | M554814 | 2/2018 |
| TW | M580447 U | 7/2019 |
| WO | WO9606664 | 3/1996 |
| WO | WO2005087323 | 9/2005 |
| WO | WO2017008775 | 1/2017 |
| WO | WO2017009775 | 1/2017 |
| WO | WO2019023473 | 1/2019 |

OTHER PUBLICATIONS

Chinese Office Action in CN Appln. No. 202080053324.5, dated Nov. 17, 2022, 10 pages (with English translation).
PCT International Preliminary Report on Patentability in International Appln. No. PCT/US2021/047249, mailed on Mar. 9, 2023, 9 pages.
'www.commonwealthmagazine.org' [online] "Bruce Smith wants to take rowing to a new level," Apr. 2015 [retrieved May 9, 2018]. Retrieved from the Internet: URL <https://commonwealthmagazine.org/environment/bruce-smith-wants-to-take-rowing-to-a-new-level/>. 25 pages.
'www.concept2.com' [online]. "Concept 2—The world's leading rowing machine," Dec. 25, 1996 [retrieved on May 9, 2018]. Retrieved from the Internet: URL http://www.concept2.com/. 2 pages.
'www.liverowing.com' [online]. "Liverowing," Feb. 2, 2011 [retrieved on May 9, 2018]. Retrieved from URL <https://liverowing.com/>. 5 pages.
'www.onepeloton.com' [online]. "The Peloton Bike: Live studio

(56) References Cited

OTHER PUBLICATIONS cycling, ready when you are," Sep. 22, 2017 [retrieved on May 9, 2018]. Retrieved from the Internet: URL <https://www.onepeloton.com/>. 9 pages.

'www.rowlab.com' [online]. "Stream Live and On-Demand Rowing Classes," 2017 [Retrieved on May 9, 2018]. Retrieved from the Internet: URL < https://rowlab.co/>. 4 pages.

'www.truerowing.com' [online]. "CREW by True Rowing: Redefining indoor workouts," [retrieved on May 9, 2018]. Retrieved from the Internet: URL <http://www.truerowing.com/>. 5 pages.

Chinese Office Action in CN Appln. No. 201980047722.3, dated Oct. 20, 2021, 18 pages with English Translation.

Flywheelsports.com [online], "Take the class of your life, your first fly is free", Published on or before May 30, 2019, retrieved on Mar. 18, 2020, retrieved from URL<https://www.flywheelsports.com/> 5 pages.

Mogan et al., "To be in synchrony or not? A meta-analysis of synchrony's effects on behavior, perception, cognition and affect," Journal of Experimental Social Psychology, 2017, 72: 13-20.

Office Action in U.S. Appl. No. 16/426,347, dated Aug. 5, 2019, 12 pages.

PCT International Preliminary Report on Patentability in International Appln. No. PCT/US2019/030646, dated Nov. 17, 2020, 10 pages.

PCT International Search Report and Written Opinion in International Application No. PCT/US2019/30646, dated Aug. 29, 2019, 18 pages.

PCT International Search Report and Written Opinion in International Appln. No. PCT/US2020/032132, dated Aug. 18, 2020, 15 pages.

PCT International Search Report and Written Opinion in International Appln. No. PCT/US2021/047249, dated Sep. 20, 2021, 10 pages.

ProForm.com [online], "Rowers", published on or before May 30, 2019, retrieved from URL<https://www.proform.com/rowing-machines/750r-rower> 15 pages.

Support.hydrow.com [online], "How the Leaderboard Works", published on Jul. 30, 2019, retrieved on Sep. 13, 2021, retrieved from URL<https://support.hydrow.corn/hc/en-us/articles/360031429651-How-the-Leaderboard-Works>.

Taiwanese Office Action in TW Appln. No. 109117615, dated Dec. 29, 2020, 19 pages with English Translation.

'www.concept2.com' [online]. "How to Use Your PM4," Aug. 28, 2012 [retrieved on Jun. 3, 2019]. Retrieved from the Internet: URL <https://www.concept2.com/service/monitors/pm4/how-to-use/viewing-drag-factor>. 2 pages.

'www.thestrokemaster.com' [online]. "The Stroke Master Elite Rowing Trainer," 2019 [retrieved on Jun. 10, 2019]. Retrieved from the Internet: https://thestrokemaster.com/products/. 6 pages.

Yogatoday.com [online], "Your Yogatoday Studio", published on or before May 30, 2019, retrieved on Mar. 18, 2020, retrieved from URL<https://www.yogatoday.com/>, 5 pages.

Japanese Office Action in JP Appln. No. 2020-564448, dated May 9, 2023, 10 pages (with English Translation).

support.hydrow.com [online], "How the Leaderboard Works," available on or before Aug. 14, 2020, via Internet Archive: Wayback Machine URL <http://web.archive.org/web/20200814060451/https://support.hydrow.com/hc/en-us/articles/360031429651-How-the-Leaderboard-Works>, retrieved on Nov. 15, 2023, retrieved from URL <https://support.hydrow.corn/hc/en-us/articles/360031429651-How-the-Leaderboard-Works>, 1 page.

support.hydrow.com [online], "How the Leaderboard Works," available on or before May 18, 2021, via Internet Archive: Wayback Machine URL <http://web.archive.org/web/20210518014852/https://support.hydrow.com/hc/en-us/articles/360031429651-How-the-Leaderboard-Works>, retrieved on Nov. 17, 2023, retrieved from URL <https://support.hydrow.corn/hc/en-us/articles/360031429651-How-the-Leaderboard-Works>, 1 page.

Notice of Acceptance in Australian Application No. 2021277676, dated Nov. 23, 2023, 3 pages.

Notice of Allowance in Japanese Application No. 2020-564448, dated Feb. 27, 2024, 5 pages (with English Translation).

Office Action in Japanese Application No. 2020-564448, dated Nov. 27, 2023, 5 pages (with English Translation).

Office Action in Korean Application No. 10-2020-7035693, dated Mar. 11, 2024, 6 pages (with English Translation).

Communication Pursuant to Article 94(3) EPC in European Application No. 19803716.0, dated Jul. 22, 2024, 8 pages.

European Search Report in European Application No. 21862523, dated Jul. 19, 2024, 8 pages.

Office Action in Taiwanese Application No. 110131160, dated Jan. 22, 2025, 70 pages (with English Translation).

\* cited by examiner

RANK LISTING OF COMPETITIVE PERFORMANCES OF EXERCISE ON A MACHINE

CROSS-REFERENCE TO RELATED APPLICATIONS

This application is a continuation application and claims priority under 35 U.S.C. § 120 to U.S. patent application Ser. No. 17/001,285, filed Aug. 24, 2020 (issued as U.S. Pat. No. 11,229,825 on Jan. 25, 2022), which is incorporated here by reference in its entirety.

BACKGROUND

This description relates to rank listing of competitive performances of exercise on a machine.

Leaderboards are a form of rank listing often used to present to competitors and observers the relative progress of leaders during and up to an end time or other end point of a competition, such as golf or track or rowing. In some kinds of competition, such as those in which the competitors use instrumented exercise machines (for example, cycling or rowing machines), progress of the competitors can be measured continuously and the results compared frequently (such as every few seconds) to show current leaderboard information. Relative performance of competitors can be reported in terms of variables such as distance covered since the start of the competition.

Exercise machines can be used in a "live" mode for live real-time competitive exercise activities, in an "on-demand" mode for virtual competitive exercise activities, or in a combination of the two.

In some uses of exercise machines in a live mode, live competitors located remotely from one another compete in real time. Live real-time video and performance data for a live competitor can be presented to the other live competitors through displays at their exercise machines to enhance their competitive experience.

In some typical uses of exercise machines in an on-demand mode, a live subject competitor engages in a virtual competition with other competitors whose prior performances for the exercise activity have been previously stored as historical performance data. The other competitors can be considered virtual competitors in that they are not competing live and in real-time but rather their historical performance data is used to create the impression of virtual competition of the virtual competitors versus the subject competitor. When such stored historical performance data is available, the subject competitor can engage in the virtual competitive exercise activity by choosing that exercise activity through a user interface of the exercise machine at a time and in a context convenient to the subject competitor. In some cases, one of the virtual competitors can be the subject competitor herself in an instance when she previously engaged in exercise activity. In other words she can be competing against her prior performance (a prior instance) of the same exercise activity.

Historical performance data for a competitor engaging in an exercise activity can include speed, distance traveled, heart rate, stroke rate, watts, and calories burned, at closely spaced exercise moments during the exercise activity.

In either an on-demand mode or a live mode of competition, an electronically determined leaderboard can be presented to the subject competitor.

SUMMARY

In general, in an aspect, a processor executes instructions to (a) during a current instance of an exercise activity having a predefined scope and being performed by a subject competitor on a machine, compute a first performance metric for the subject competitor using performance data from the subject competitor's performance of a lesser scope than the predefined scope of the current instance of the exercise activity, the first performance metric being normalized to reflect a hypothetical performance over the predefined scope, (b) receive performance data representing an historical performance during a previous instance of the exercise activity by at least one other competitor on a machine, and (c) present to the subject competitor comparative data based on the first performance metric and on a second performance metric for the historical performance by at least one other competitor that is based on the received performance data and that reflects performance of the at least one other competitor of a scope of the previous instance that is substantially the same as the predefined scope.

Implementations can include one or a combination of two or more of the following features. The exercise activity includes rowing. The predefined scope includes a time duration. The predefined scope includes a distance. The machine includes a rowing machine. The performance metric includes a distance predicted to be covered during the predefined scope of the exercise activity. The performance data includes distance data. The performance metric includes a time predicted to have elapsed for the predefined scope of the exercise activity. The performance metric includes an average speed as of a current exercise moment. The subject competitor's performance of less than the predefined scope includes the subject competitor's performance for a time duration shorter than a time duration of the predefined scope. The comparative data includes a predicted value of the first performance metric for the subject competitor. The predicted value of the first performance metric includes a predicted distance. The predicted value of the first performance metric for the subject competitor is based on an actual value of the first performance metric for the subject competitor's performance of the lesser scope. The predicted value of the first performance metric for the subject competitor is based on an actual value of the second performance metric for the historical performance by at least one other competitor's performance of the lesser scope. The predicted value of the first performance metric for the subject competitor is based on the proportion of the predefined scope represented by the lesser scope. The predicted value of the first performance metric is based on a rank of the subject competitor based on the subject competitor's performance of the lesser scope. Presenting the comparative data includes displaying the comparative data in an interactive user interface accessible to the subject competitor. Presenting the comparative data includes presenting data representing a performance of the subject competitor and data representing a relative performance of at least one other competitor compared to the subject competitor. The at least one other competitor is a live competitor in the current instance of the exercise activity and the received performance data is of the historical performance of the live competitor during a previous instance of the exercise activity.

In general, in an aspect, a processor executes instructions to (a) receive from an exercise machine current performance data indicative of a performance metric for a subject competitor performing a current instance of an exercise activity having a predefined scope, the current performance data being indicative of a performance metric for a lesser scope than the predefined scope, (b) receive historical performance data representing an historical performance during a previous instance of the exercise activity by at least one other competitor on a machine, and (c) use the current performance data and the historical performance data to compute the performance metric including normalizing the performance metric to represent a hypothetical performance of the subject competitor over the predefined scope.

Implementations can include one or a combination of two or more of the following features. The exercise activity includes rowing. The predefined scope includes a time duration. The machine includes a rowing machine. The performance metric includes a distance predicted to be covered during the predefined scope of the exercise activity. The current performance data and the historical performance data include distance data. The current performance data is indicative of a performance metric for the subject competitor's performance of less than the predefined scope. The performance metric includes a predicted performance metric for the predefined scope. The predicted performance metric for the subject competitor is based on an actual value of the performance metric for the subject competitor's performance of the lesser scope. The predicted performance metric for the subject competitor is based on an actual value of the historical performance of the lesser scope by at least one other competitor. The predicted performance metric for the subject competitor is based on the proportion of the predefined scope represented by the lesser scope. The performance metric of the subject competitor is presented. The historical performance by at least one other competitor on a machine is presented.

In general, in an aspect, a processor executes instructions to (a) during a current instance of an exercise activity having a predefined scope and being performed by a subject competitor on a machine, compute a performance metric for the subject competitor using performance data from the subject competitor's performance of a lesser scope than the predefined scope of the current instance of the exercise activity, and (b) apply a straight-line projection to the performance metric for the lesser scope projection to predict the performance metric for the predefined scope of the exercise activity.

Implementations may include one or a combination of two or more of the following features. The exercise activity comprises rowing. The predefined scope comprises a time duration. The machine comprises a rowing machine. The performance metric comprises a distance predicted to be covered during the predefined scope of the exercise activity. The performance data comprises distance data. The subject competitor's performance of less than the predefined scope comprises the subject competitor's performance for a time duration shorter than a time duration of the predefined scope. The predicted performance metric comprises a predicted distance. The predicted performance data is displayed in an interactive user interface accessible to the subject competitor.

These and other aspects, features, implementations, and advantages (a) can be expressed as methods, apparatus, systems, components, program products, business methods, means or steps for performing functions, and in other ways, and (b) will become apparent from the following description and from the claims.

DESCRIPTION

Figure 2:
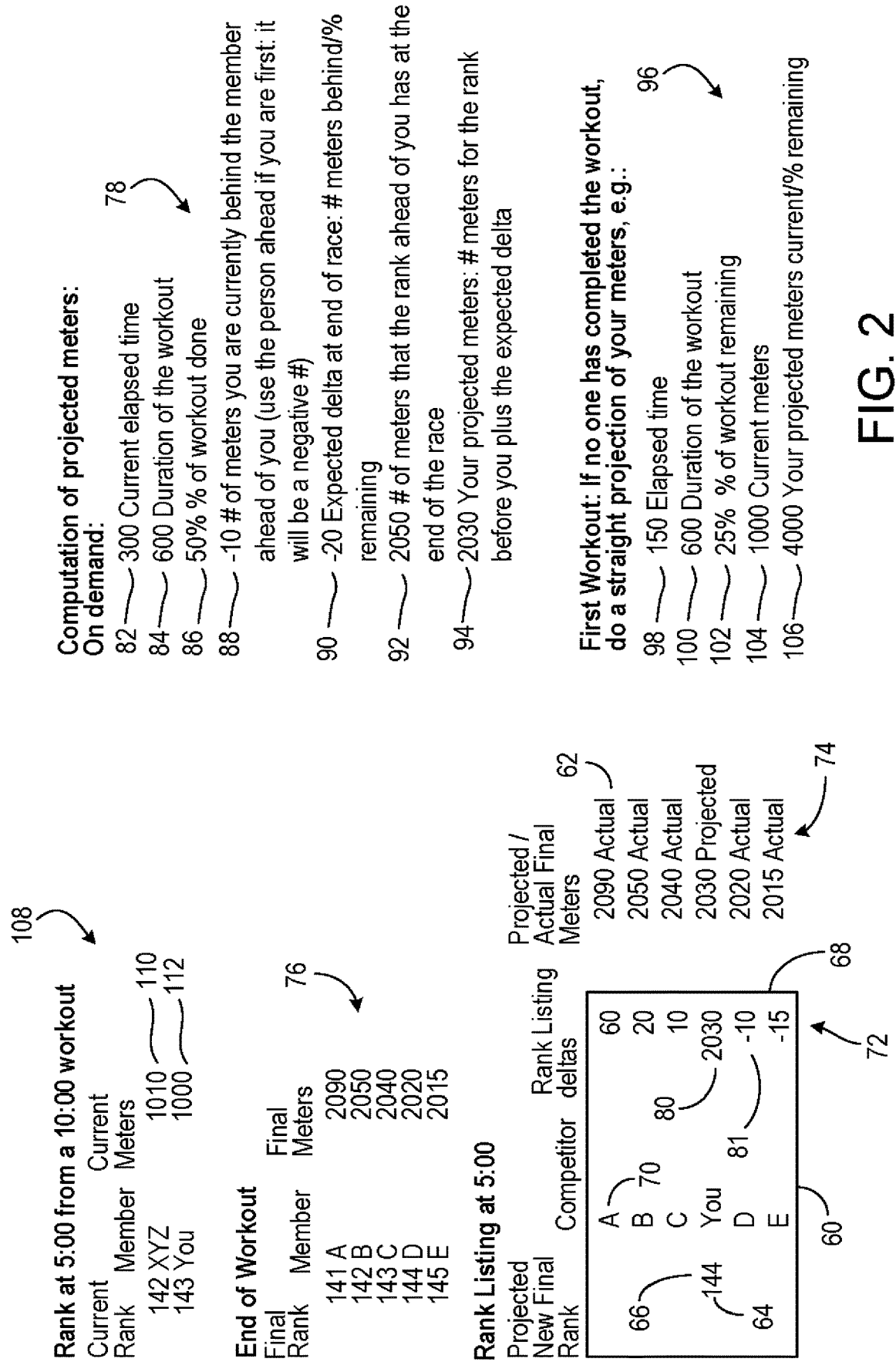
Figure 3:
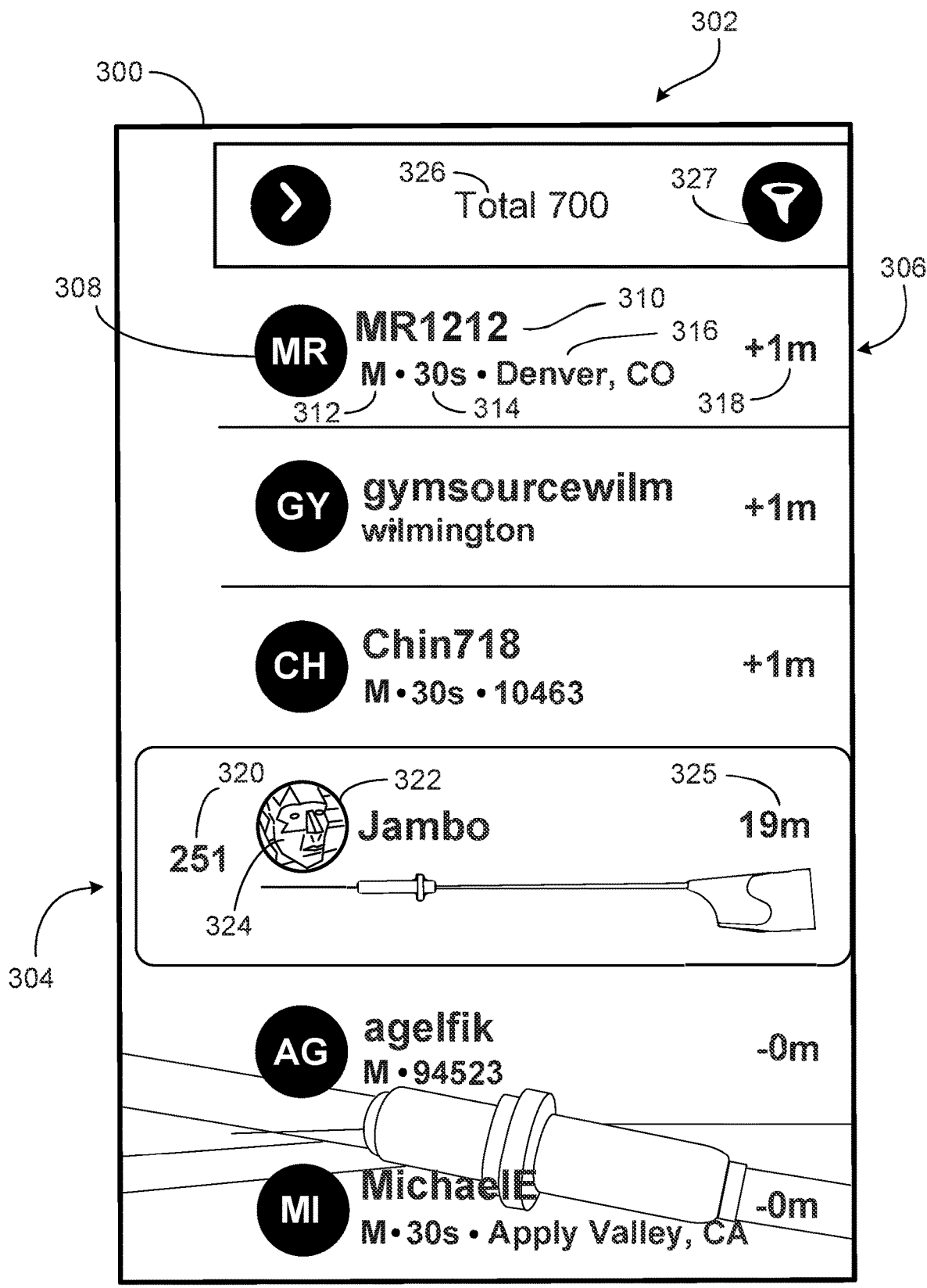

FIG. 1 is a block diagram.
FIG. 2 is a table including a rank listing.
FIG. 3 is a user interface.

As shown in FIG. 1, here we describe a rank listing technology 10 that can be used to generate (and present) rank listings 12 of competitors engaged in an exercise activity. The competitors can include a current subject competitor 14 engaged in, for example, an on-demand mode exercise activity on an exercise machine 16, one or more virtual competitors 18, and, in some cases, one or more other current competitors 20, concurrently or previously engaged in the same exercise activity on exercise machines 22, 24. (Note that in some implementations, the performances of other current competitors will not be included in the presented rank listing unless and until they reach the end of the exercise activity.) Each of the exercise machines can be equipped with electronic instruments 26 to measure and generate performance data for each of the competitors with respect to one or more performance metrics 28 for the exercise activity. We sometimes refer to an occasion on which a subject competitor or a virtual competitor engages in an exercise activity as an "instance".

In some cases, when the exercise machine is a rowing machine, the linear motion of the handle is converted to rotary motion through a drivetrain. Drivetrain components are coupled to rotary encoders to produce electronic signals proportional to changes in angle of a rotating shaft. The signals are monitored at regular time intervals by a microcontroller, which is therefore able to compute position, velocity, and acceleration of the rotating components. Measured angular motion is then used to generate exercise performance metrics according to a physical model of the functioning of the exercise machine. Distance, one specific performance metric that can be computed for a rowing machine, is a function of the amount of rotation measured from the machine's flywheel and the amount of braking torque imposed by the rowing machine to decelerate the flywheel. A rower is determined to have covered more distance if she is producing more watts while rowing.

The measured performance data can be used immediately as an indicator of the subject competitor's performance, or can be stored as historical performance data for later use in representing a virtual competitor during a competition.

The rank listings can be generated by a processor 29 executing instructions 31 stored on a tangible storage 33 using real-time performance data 30 for the subject competitor and any of the other current competitors and using stored historical performance data 32 for any of the virtual competitors. (Note that in some implementations, the performances of other current competitors will not be included in the presented rank listing unless and until they reach the end of the exercise activity.) The processor and tangible storage can be located at a server 35 which communicates through the Internet or other communication network 37 with the electronic instruments at the exercise machines. In some cases, the electronic instruments can include or be controlled by a computational device 39 such as a dedicated computer or a portable smart phone or tablet. A display 41 on the computational device can be used to present the rank listing to the subject competitor or another live competitor. The server can send the rank listing or information to generate the rank listing through the network to the computational device for presentation through a user interface shown on the display.

The rank listing can include a list of two or more entries 34, each for a corresponding competitor. Each entry on the rank listing can include an identifier 42 of the competitor and indicators 43, 45 of the competitors' relative performances at one or more times 53 ("exercise moments") during the exercise period 51 of the exercise activity (that is, the period beginning with the start 47 and ending with the finish 49 of the exercise activity). For this purpose, the indicators of relative performances can be of predicted performance metrics for the subject competitor and of historical final metrics for the virtual competitors. We sometimes refer to the exercise period as a "predefined scope" of the exercise activity. When an exercise moment occurs before the end of the exercise period (that is, before the end of the "predefined scope"), we sometimes refer to the period from the start of the exercise activity to the current exercise moment as a "lesser scope". In some examples, the exercise activity may be considered to have been completed when a final distance (say 5000 meters) or a final time period (say 5 minutes) has been reached. Yet the predefined scope could be shorter in distance (say 4000 meters) or in time (say 4 minutes) and the lesser scope would be shorter in distance or time than the predefined scope.

A variety of performance metrics can be used for measuring the relative performances of two or more competitors for a given type of exercise activity and for reporting their relative performance in a rank listing at each of a succession of performance moments. One such performance metric is a distance covered on a real or hypothetical exercise course associated with the exercise activity (for example, a running, cycling, or rowing course) for a given period of time (the "predefined scope"). Various distance metrics could be used, such as an interim distance covered by a competitor from the start of the exercise period and up to a particular exercise moment (for example, a "lesser scope"), a final distance covered by the competitor for the entire exercise period (the "predefined scope"), a predicted distance anticipated to be covered by a competitor as of a particular future exercise moment, or a predicted final distance anticipated to be covered by a competitor for an entire exercise period. In some cases, the performance metric could be the amount of time that elapses for the competitor to cover a predefined distance. Other parameters for the performance metric and predefined scope could also be used such as the average speed as of a current exercise moment In the latter case, the subject competitor's average speed as of the current exercise moment can be presented on the rank listing with the final average speeds of the virtual competitors.

In an on-demand mode, the rank listing can report the performances of a subject competitor and of one or more virtual competitors even though the subject competitor is not then one of the top performers. In other words, the rank listing need not be a literal leaderboard in the sense that the rank listing may not report the performances of the top-performing competitors. In some examples, however, the virtual competitors identified on the rank listing may include the virtual competitors who had the best performances or the virtual competitors whose performances are next above or next below the subject competitor in rank. In some cases, the choice of which virtual competitors to present can be selected in other ways. In some instances, the subject competitor can specify through a user interface the competitors whose performances should be shown on the rank listing with the subject competitor.

Computation and Reporting of Performances and Ranks in an On-Demand Mode

As shown by example in FIG. 2 for an exercise activity that is a 10-minute rowing exercise, the rank listing is shown as of the 5-minute exercise moment, halfway through the exercise activity. The rank listing could be updated at regular frequent intervals, for example, every second, two seconds, ten seconds, or minute. Using two seconds renders the rank listing current enough for a typical competitor but not so frequent as to be jarring.

The rank listing 60 shows the projected rank 66 of the subject competitor (called "you"). In this case, the predicted rank is $144^{th}$ as of this exercise moment. The rank listing also includes entries 68 for five other competitors, in this case virtual competitors. Each of the virtual competitors is identified by a letter 70. For each of the virtual competitors, the rank listing shows the differential distance 81 (in this case in meters) by which the virtual competitor is anticipated to be ahead of or behind the subject competitor as of the end of the exercise period. Column 72 also shows the anticipated distance that the subject competitor will have rowed at the end of the exercise period (e.g., the end of the "predefined scope"), in this case 2030 meters.

As a result the subject competitor in an on-demand exercise activity will see, and easily and quickly be able to evaluate, her predicted rank as of the end of the exercise period (predefined scope), how far she can expect to have rowed at the end of the exercise period, and how far (in distance) she will then be ahead or behind or even with a selected number of identified virtual competitors who have previously completed the same exercise activity. Column 74, which may or may not be reported on the rank listing, shows the actual distance rowed by each of the virtual competitors for the full exercise period, according to the historical performance data.

Table 76 of FIG. 2 shows historical performance data for the five virtual competitors covered by the rank listing, namely the five virtual competitors whose actual historical performance data for distance rowed as of the end of the exercise activity is closest to (above or below) the anticipated distance rowed by the subject competitor. The part of the rank listing 60 that shows distance differences for the virtual competitors compared to the subject competitor can be created from the data in table 76.

Table 78 of FIG. 2 shows the steps in calculating the value 80 of the rank listing 72, that is, for generating a predicted final distance of the subject competitor. In this example, the current elapsed time is 300 minutes (line 82). The exercise period is 600 minutes (line 84). The part of the workout that is done is 50% (line 86). Other approaches can also be used for generating predicted final distances.

The number of meters that the subject competitor is currently behind the next best performing virtual competitor is −10 meters (line 88). Line 88 is determined by subtracting, from the distance covered by the subject competitor determined at 5:00 (in this case 1000 meters, line 112), the known distance covered by the virtual competitor as of 5:00 into the exercise period (in this case 1100 meters, line 110 of table 108).

Line 90 is the anticipated difference as of the end of the exercise period, calculated as the number of meters that the subject competitor is behind the next best performing virtual competitor divided by the percentage of the exercise period completed (in this example, 50%).

Line 90 is the number of meters that the virtual competitor who is next ahead of the subject competitor covered by the end of the exercise period based on historical performance data (in this case, 2050). Line 92 is the subject competitor's number of meters at the end of the exercise period net of the difference shown in line 90 (that is, 2030=2050−20).

In this example, the subject competitor is in 143rd place at 5:00 and is projected to have fallen in rank by one position to 144th as of the end of the exercise activity.

Historical Performance Data

In some cases, the technology maintains historical performance data for every competitor who has participated in an instance of the particular exercise activity for use (among other things) in reporting information on the rank listing in future competitions. The number of such competitors for whom historical performance data is stored could be any number from 0 to a very large number (hundreds or even thousands or millions).

If no one has previously participated in the particular exercise activity and the subject competitor is the first to do so, the predicted final distance of the subject competitor's performance can be calculated as shown in table 96 for an example in which the calculation is being made as of 25% (line 102, that is, 150 seconds, line 98) into the 600-seconds exercise period (line 100). The measured distance covered as of that moment is 1000 meters (line 104) and the predicted final distance is the current distance divided by the percentage of completion (line 106, 4000=1000/25%). In effect the server uses a straight-line projection. Other mathematical operations could be used to generate a prediction based on, for example, workout intensity, stroke rate, historical data, or other information. The subject competitor will be the only competitor shown on the rank listing.

User Interface Presentation

As shown in FIG. 3, in some implementations, the presentation of the rank listing 300 on a user interface 302 includes an entry 304 for the subject competitor and entries 306 for each of five virtual competitors two of whom are ranked immediately lower and three of whom are ranked immediately higher than the subject competitor. The entry for each virtual competitor presents a badge 308 including the first two characters of the pseudonym, and a set of information about the virtual competitor including a pseudonym 310, gender 312, age bracket 314, and address indicator 316. At the right end of the entry is a differential distance number 318 representing a difference between the actual historical final distance of the virtual competitor and the predicted final distance of the subject competitor. In the example shown, three virtual competitors each had an actual historical final distance 1 meter ahead of the predicted final distance of the subject competitor and two virtual competitors each had an actual historical final distance the same as the predicted final distance of the subject competitor.

In some cases, the badge can contain an avatar with a photograph of the competitor (or any other image) and/or an oar blade representing that competitor's affiliation.

The entry 304 for the subject competitor shows his current rank 320, a badge 322 showing an image 324, and a predicted final distance 325. The total number of virtual competitors 326 is shown at the top of the user interface presentation.

In addition to presenting to the subject competitor her predicted final distance in conjunction with differential distances for the virtual competitors, the user interface can provide an option for showing the subject competitor's actual distance covered as of the exercise moment being presented. Note that, in FIG. 3, the actual distance option is presented using the number 19 m.

The user interface includes a filter button 327 that enables the user to filter the entries on the rank listing according to gender or decade of age (e.g., 50s, 30s). Filtering could be done on any other arbitrary attributes such as rower affiliation, geographic location, or interests, among other things. Then the subject competitor's rank according to her predicted final distance can be determined based on all competitors, but the rank listing can present only the filtered members.

This should provide bigger samples for better estimates of rank for new exercise activities having few virtual competitors, and for less common filters; e.g., non-binary 70+. A straight-line prediction of the subject competitor's final distance might be used instead.

Effects of the Technology

The rank listing described above reflects the subject competitor's current rank in the exercise activity at each successive exercise moment, and gives the subject competitor the advantage of knowing the final distance she will need to achieve to beat the virtual competitors who have nearby ranks. The presented ranks of the virtual competitors are static and do not change throughout the exercise activity because they reflect fixed historical performance data. Only the rank of the subject competitor relative to the virtual competitors can change as a result of, for example, greater or lesser effort exerted by the subject competitor.

Using the subject competitor's current rank as the basis of prediction of the subject competitors final distance should be more stable than using a straight line projection technique, for exercise activities that have varying intensities during the exercise period (e.g., HIIT: High-Intensity Interval Training, warm ups, or cool downs). One explanation for determining the predicted final distance using a current rank of a subject competitor is that it takes into consideration that competitors are applying the same exercise structure and will tend to vary their speeds similarly. By contrast, a straight line projection could be misleading and unstable because the subject competitor will tend to drop in rank during "off intervals" and gain in rank during "on intervals." Also, during a warm up period of an exercise activity, the subject competitor's average speed will be slower than the average speed for the full exercise activity. If a straight line projection technique were used in those circumstances, the projection could be misleadingly poor during a warm up period.

Alternatives

Other implementations are within the scope of the following claims.

For example, although the earlier description has used rowing examples, the technology is also applicable to other kinds of exercise equipment and exercise activities, such as cycling, walking, and running, or other activities in which distance is a performance metric.

In some implementations, the technology could be used for any sport or activity involving "historical competitors" who are "in the clubhouse" competing with active competitors. The technology could be used for televised or broadcast activities as well as activities presented on the internet (such as ESPN.net). The technology could also be used for online gaming, such as racing games.

Communication architectures other than client-server could be applied in some implementations, including peer-to-peer architectures, for example.

The predefined scope could be a distance rather than a time, or could be one or more other parameters. The performance metric includes a time predicted to have elapsed for the predefined scope of the exercise activity. The performance metric could be one or more other parameters.

In some cases, the rank listing can present a ranked list of performances according to the performance metrics without presenting any identifying information about the one or more of the virtual competitors for whom the ranked performance metrics are presented.

In some examples, the rank listing technology can be applied to competitions in which the subject competitor is competing against one or more other live competitors who are performing the exercise activity in real time with the subject competitor. In some instances, one or more virtual competitors also can be included. We sometimes refer to such competitions as occurring in "live mode." In live mode, although the technology cannot predict the performance of another live competitor based on her final data on the current exercise activity, the technology can predict that performance based on her past performance of the exercise activity.

The invention claimed is:

1. An exercise machine comprising:
    a movable mechanical element;
    a sensor configured to measure motion of the movable mechanical element, wherein the measured motion is indicative of performance data for a current instance of an exercise activity by a subject competitor using the exercise machine;
    a display device; and
    a computing device, operably connected to the sensor and the display device, configured to transmit and receive performance data with at least one other exercise machine over a network, the computing device further configured to:
    update, in real time during the current instance of the exercise activity by the subject competitor, a graphical user interface displayed on the display device,
    wherein the updated graphical user interface comprises:
        a ranking of the subject competitor and a second competitor based on (i) a projected performance metric of the subject competitor over a predefined scope of the exercise activity, the projected performance metric based on the performance data, in comparison to (ii) a historical performance metric of the second competitor over the predefined scope of the exercise activity in a previous instance of the exercise activity,
            wherein the graphical user interface is updated at a time when the subject competitor has completed a lesser scope than the predefined scope of the exercise activity,
        an illustration of a margin between the historical performance metric of the second competitor and the projected performance metric for the subject competitor, and
        an illustration of the projected performance metric, and
    wherein the update of the graphical user interface comprises:
        receiving, by the computing device, from a remote server through the network, information relating to an update to at least one of the ranking, the margin, or the projected performance metric, and
        updating, by the computing device, the at least one of the ranking, the margin, or the projected performance metric based on the received information.

2. The exercise machine of claim 1, wherein the sensor comprises a rotary encoder configured to measure a rotation of the movable mechanical element.

3. The exercise machine of claim 2, wherein the movable mechanical element comprises a shaft, and wherein the rotary encoder is configured to produce a signal proportional to a change in an angle of the shaft.

4. The exercise machine of claim 3, further comprising a microcontroller configured to use the produced signal to determine at least one of a position, velocity, or acceleration of the movable mechanical element.

5. The exercise machine of claim 1, wherein the updated graphical user interface comprises a grid-formatted display along a first dimension and a second dimension,
    wherein an order in which the subject competitor and the second competitor are presented along the second dimension is based on the ranking, and
    wherein a linear display along the second dimension includes:
        in a first line along the first dimension corresponding to the second competitor, the margin between the historical performance metric of the second competitor and the projected performance metric for the subject competitor, and
        in a second line along the first dimension corresponding to the subject competitor, the projected performance metric.

6. The exercise machine of claim 1, wherein the projected performance metric comprises a time or a distance.

7. The exercise machine of claim 1, wherein the updated graphical user interface further comprises a user interface element selectable to filter competitors from the ranking.

8. The exercise machine of claim 1, wherein the updated graphical user interface further comprises an option to display a current performance metric of the subject competitor.

9. The exercise machine of claim 1, wherein the movable mechanical element comprises a drivetrain component.

10. The exercise machine of claim 1, wherein the performance data is a function of the measured motion and an amount of torque imposed by the exercise machine.

11. A system comprising:
    the exercise machine of claim 1, and
    the remote server, wherein the remote server is configured to calculate the projected performance metric, and wherein calculating the projected performance metric comprises:
        identifying the second competitor as a competitor whose historical performance data over the lesser scope is next-best, among historical performance data of a plurality of virtual competitors, compared to current performance data of the subject competitor over the lesser scope; and
        based on identifying the second competitor as the competitor whose historical performance data over the lesser scope is next-best compared to the current performance data of the subject competitor, calculating the projected performance metric based on the historical performance data of the second competitor over the lesser scope, the current performance data of the subject competitor over the lesser scope, and a proportion of the predefined scope represented by the lesser scope.

12. A system comprising:
    the exercise machine of claim 1, and
    the remote server, wherein the remote server is configured to determine the ranking and the information relating to the update to the at least one of the ranking, the margin, or the projected performance metric.

* * * * *